(12) United States Patent
Li et al.

(10) Patent No.: US 11,001,855 B2
(45) Date of Patent: May 11, 2021

(54) RICE PLANTHOPPER-SENSITIVITY GENE BGIOSGA015651 AND USE THEREOF

(71) Applicant: Plant Protection Research Institute, Guangdong Academy of Agricultural Sciences, Guangdong (CN)

(72) Inventors: Yifeng Li, Guangdong (CN); Zhenfei Zhang, Guangdong (CN); Hanxiang Xiao, Guangdone (CN); Yanfang Li, Guangdong (CN); Yang Zhang, Guangdong (CN)

(73) Assignee: PLANT PROTECTION RESEARCH INSTITUTE, GUANGDONG ACADEMY OF AGRICULTURAL SCIENCES, Guangdong (CN)

( * ) Notice: Subject to any disclaimer, the term of this patent is extended or adjusted under 35 U.S.C. 154(b) by 0 days.

(21) Appl. No.: 16/324,112

(22) PCT Filed: Mar. 9, 2018

(86) PCT No.: PCT/CN2018/078591
§ 371 (c)(1),
(2) Date: Feb. 7, 2019

(87) PCT Pub. No.: WO2018/205732
PCT Pub. Date: Nov. 15, 2018

(65) Prior Publication Data
US 2020/0140883 A1   May 7, 2020

(30) Foreign Application Priority Data

May 8, 2017 (CN) .......................... 201710317773.6

(51) Int. Cl.
*C12N 15/82* (2006.01)
*C07K 14/415* (2006.01)

(52) U.S. Cl.
CPC ........ *C12N 15/8286* (2013.01); *C07K 14/415* (2013.01)

(58) Field of Classification Search
CPC .......................... C12N 15/8286; C07K 14/415
See application file for complete search history.

(56) References Cited

FOREIGN PATENT DOCUMENTS

| CN | 101463354 A | 6/2009 |
|---|---|---|
| CN | 101967486 A | 9/2011 |
| CN | 104099342 A | 10/2014 |
| CN | 105820222 A | * 8/2016 |
| CN | 107034223 A | 8/2017 |
| WO | WO 2003008540 | * 1/2013 |

OTHER PUBLICATIONS

Feng et al (Sequence and analysis of rice chromosome 4. Nature 420:316-320, 2002) (Year: 2002).*
Yu et al (The Genomes of *Oryza sativa*: A History of Duplications. PloS Biology 3: 0266-0281, 2005) (Year: 2005).*
Feng et al (Sequence and analysis of rice chromosome 4. Nature, 316-320, 2002) (Year: 2002).*
Yu et al (The genomes of *Oryza sativa*: a history of duplications. PLoS Biol.3:266-281, 2005) (Year: 2005).*
Feng, Q., et al., "GenBank Accession CR855031.1", document available at: https://www.ncbi.nlm.nih.gov/nuccore/CR855031.1/#; retrieved on Dec. 28, 2018.
Yu, J., et al., "GenBank Accession EAY92929.1", document available at: https://www.ncbi.nlm.nih.gov/protein/EAY92929#; retrieved on Dec. 28, 2018.
Yu, J., et al., Advances in Inheritance and Mapping of Rice Genes Resistant to Plant Hoppers; Journal of Plant Genetic Resources, 2011, 12(5): 750-756.
Ma, L., et al., "An analysis of transcriptional regulation of the rice genome and its comparison to *Arabidopsis*", Department of Bioinformatic Beijing Institute of Genomics Chinese Academy of Sciences, Beijing, China, document available at: https://www.ebi.ac.uk/ena/data/view/CL967978&display=text.
Huang, Z., et al., "Identification and Mapping of Two Brown Planthopper Resistance Genes in Rice" Theoretical and Applied Genetics, May 2001, vol. 102, Issue 6-7, pp. 929-934.

* cited by examiner

*Primary Examiner* — Ashley K Buran
*Assistant Examiner* — Wayne Zhong
(74) *Attorney, Agent, or Firm* — McNees Wallace & Nurick LLC

(57) ABSTRACT

The present disclosure provides a rice planthopper-sensitivity gene BGIOSGA015651 and the use thereof. The applicant found a gene BGIOSGA015651 for regulating rice planthopper-resistance by studying on rice varieties BG1222 and TN1. The gene expression level of BGIOSGA015651 in the insect-resistant variety is hundreds of times or more different from that of the insect-susceptible variety. The expression of this gene can be reduced or knocked out by molecular breeding methods or genetic engineering methods, resulting in that the insect-susceptible plant can obtain high insect-resistance. The resistance level of the insect-susceptible rice variety TN1 is of level 9 before knock-out, and the resistance level thereof is significantly increased to level 0-1 after the rice planthopper-sensitivity gene BGIOSGA015651 is knocked out. The gene and the encoded protein thereof can be used for plant genetic improvement, and the obtained rice for breeding can be widely promoted in a wide range of rice growing areas, and has high economic values and outstanding ecological benefits.

10 Claims, 1 Drawing Sheet
Specification includes a Sequence Listing.

RICE PLANTHOPPER-SENSITIVITY GENE BGIOSGA015651 AND USE THEREOF

PRIORITY

The present application is U.S. National Stage Patent Application under 35 USC 371 which claims priority to Patent Cooperation Treaty Patent Application PCT/CN2018/078591, filed Mar. 9, 2018, which claims priority to and benefit of Chinese Application No. 201710317773.6, CN, filed May 8, 2017, each with the title "RICE PLANTHOPPER-SENSITIVITY GENE BGIOSGA015651 AND USE THEREOF," each of which is hereby incorporated by reference in their entirety.

TECHNICAL Field

The present invention belongs to the field of molecular biology and agriculture, and particularly relates to a rice planthopper-sensitivity gene BGIOSGA015651 and the use thereof.

BACKGROUND

With entry into the post-genomic era, comprehensive research in functional genomics has become a frontier field of life science research. Rice is considered as a model plant, because the transgenic technology for rice is relatively easy and its genome has colinearity with those of other gramineous crops. At present, the fine genetic and physical maps of rice genome have been completed. Further research on rice functional genes is of great significance for socio-economic development and biological research.

Nowadays, more than half of the world's population mainly lives on rice. Food security is a challenge for people all over the world. Two technological revolutions, such as dwarf breeding in 1950s, 1960s and hybrid rice breeding in 1970s, have significantly improved rice yields. However, in recent decades, rice is suffering from widespread diseases and insect pests, which are threatening the rice yields. Brown planthopper (*Nilaparvata lugens*) is a major pest which damages rice production in China. Its adults and nymphs suck rice juice with their stylets, which leads to yellow leaves or dead, and then to reduced yields or total crop failure. As recorded in CHINA AGRICULTURE YEARBOOK, the brown planthopper outbroke nationwide in 1966, 1969, 1973, 1977, 1983 and 2003, and massively outbroke nationwide in 1987, 1991, 2005, 2006 and 2007, which damaged up to over 50% of the total rice area, resulting in a severe loss in the rice production of China.

At present, the brown planthopper has become the first one among the insect pests against the rice production of China, and seriously threatens the food security of China. The prevention and control of the brown planthopper, for a long time, mainly depends on the administration of chemical insecticides. Since the outbreak of the brown planthopper occurs mostly during the grain filling period of rice and rice plants grow vigorously in this period, it is very difficult to apply the insecticides to the bases of the rice plants. Moreover, the insecticide resistance of the brown planthopper has been multiplied due to the large-scale administration of the chemical insecticides for several successive years, and the chemical insecticides have very limited preventing and controlling effects. At the same time, using the chemical insecticides to control the brown planthopper not only increases the production costs of farmers, but also leads to environmental and ecological problems such as poisoning non-targeted organisms to death, pollutions to environment and food, and the like.

A method of breeding insect-resistant rice varieties with a brown planthopper-resistant gene is most economical and effective for comprehensive preventing and controlling the brown planthopper. It is demonstrated by the research results of International Rice Research Institute (IRRI) and rice productive practices in Southeast Asia that a rice variety only having a moderate resistance level is sufficient to control the population levels of the brown planthopper below those capable of causing hazard, thereby not leading to actual hazard and loss of rice production. Therefore, a fundamental measure for preventing and controlling rice brown planthopper would be developing a rice brown planthopper-resistant gene and applying it in rice breeding projects.

Since the 1960s, researches have been performed on the inheritance and breeding of the brown planthopper-resistance. However, insect-resistant varieties are facing the risk of shortened service life and resistance loss, as new biotypes (or new harmful-types) appear. For example, the International Rice Research Institute launched a variety IR26 having Bph1 gene in 1973, but a harmful biotype 2 was found 2-3 years later. In 1977-1978, varieties IR36 and IR42 having Bph2 resistant gene were launched, but new biotypes of the brown planthopper appeared in some countries successively in 1982. Thus, new resistant varieties IR56 and IR64 had to be bred correspondingly in 1983. In addition, a considerable part of rice varieties, which commonly had high-resistant levels, has become to ones moderately resistant or even susceptible to insects.

In addition to the brown planthopper, there are other common species of planthoppers that are harmful to rice, such as *Sogatella furcifera* and *Laodelphax striatellus*. Among them, the brown planthopper has long-distance migration habits and is currently the primary pest to rice in China and many other Asian countries. *Sogatella furcifera* infection occurs in all rice regions throughout China. In addition to directly sucking juice of rice, *Sogatella furcifera* also acts as a main media for spreading rice viral diseases. In the prior art, some developed resistant rice varieties mainly have resistance to the brown planthopper, but have uncertain or no resistance to *Sogatella furcifera*, which affects the application scope of these resistant rice varieties.

Therefore, it is of great importance to continuously in-depth screen and study resistant resources, search for new resistant genes, map and clone related genes thereof, and develop new rice varieties which have genetic materials of high resistance and can be applied in wide regions.

SUMMARY

The object of the present invention is to provide a rice planthopper-sensitivity gene BGIOSGA015651 and use thereof.

The technical solution adopted by the present invention is as follows:

A rice planthopper-sensitivity gene BGIOSGA015651, which may comprise a nucleotide sequence as shown by SEQ ID NO: 1 or 2, or a homologous sequence which has at least 90% or more identity with SEQ ID NO: 1 or 2.

A cDNA of a rice planthopper-sensitivity gene BGIOSGA015651, which may comprise a nucleotide sequence as shown by SEQ ID NO: 3 or 4, or a homologous sequence which has at least 90% or more identity with SEQ ID NO: 3 or 4.

A protein for regulating the planthopper-resistance of rice, which may comprise an amino acid sequence as shown by SEQ ID NO: 5 or 6.

A nucleotide sequence encoding the protein for regulating the planthopper-resistance of rice, as described above.

Preferably, the nucleotide sequence may be selected from a group consisting of SEQ ID NOs: 1-4, or a sequence which is obtained by a substitution, deletion or addition of one or more nucleotides of SEQ ID NOs: 1-4, and encodes the same amino acid sequences as that encoded by SEQ ID NOs: 1-4.

The use of rice planthopper-sensitivity gene BGIOSGA015651 in breeding of planthopper-resistant rice, the nucleotide sequence of gene BGIOSGA015651 may be selected from a group consisting of SEQ ID NO: 1, SEQ ID NO: 2, a homologous sequence which has at least 90% or more identity with SEQ ID NO: 1 and/or 2, SEQ ID NO: 3, SEQ ID NO: 4, and a homologous sequence which has at least 90% or more identity with SEQ ID NO: 3 and/or 4.

The rice planthopper-sensitivity gene BGIOSGA015651 is positioned at 2,507,775-2,510,316 on chromosome 4 of the genome of *Oryza sativa Indica*, and has 2542 bp in total.

Preferably, the planthopper may comprise *Nilaparvata lugens* and *Sogatella furcifera*.

A method for improving the planthopper-resistance of rice, the method may include knocking out or reducing the expression level of the gene BGIOSGA015651 as described above to improve the planthopper-resistance of the rice.

The gene BGIOSGA015651 is one that may regulate the planthopper-resistance of the rice, may have a nucleotide sequence as shown by SEQ ID NO: 1 or 2, and may be positioned at 2,507,775-2,510,316 on chromosome 4 of the genome of *Oryza sativa Indica*, and may have 2542 bp in total.

Preferably, the expression level of the gene BGIOSGA015651 may be knocked out or reduced by a molecular breeding or genetic engineering method.

Preferably, the genetic engineering method may include RNA interference and gene editing.

Preferably, the planthopper may comprise *Nilaparvata lugens* and *Sogatella furcifera*.

The beneficial effects of the present invention are as follows:

The applicant of the present invention found a gene for regulating the planthopper-resistance of rice by studying on a rice variety BG1222 that has stable resistance to the brown planthopper and a rice variety TN1 that is susceptible to insects. This gene was sequenced and named as BGIOSGA015651. It was found that the gene expression level of BGIOSGA015651 in the insect-resistant variety is significantly different from that of the insect-susceptible variety. The expression level of BGIOSGA015651 in the insect-resistant variety BG1222 is hundreds or more of times lower than that of the insect-susceptible rice variety TN1. The expression level of BGIOSGA015651 in BG1222 is much lower than that of TN1, regardless if it is sucked by the brown planthopper. For previously discovered planthopper-resistant genes, their expression or even high expression is required, in order to produce insect resistance. In contrast, the rice planthopper-sensitivity gene BGIOSGA015651 of the present invention can produce good insect-resistance in BG1222, even if it is expressed at an extremely low level or is not expressed (by gene knockout).

It is demonstrated by hybrid $F_2$ progeny verification that the expression level of BGIOSGA015651 is negatively related to the insect-resistance of rice (i.e., the lower the expression level, the stronger the insect resistance). In the progeny, the stronger the insect resistance, the smaller the resistance score (Grade), and correspondingly the lower the expression level of BGIOSGA015651.

The gene BGIOSGA015651 is knocked out by gene editing technology to delete the expression of the gene BGIOSGA015651 in TN1. As a result, the insect-susceptible rice variety TN1 can obtain insect-resistance as high as that of the rice variety BG1222, and exhibits a high resistance level to *Nilaparvata lugens* and *Sogatella furcifera*. Among them, the resistance of the insect-susceptible rice variety TN1 is at level 9 before the gene BGIOSGA015651 is knocked out, and the resistance thereof is significantly increased to level 0 to 1 (high resistance level) after the gene BGIOSGA015651 is knocked out. With a bulk test of seedlings, the applicants found that the varieties, which previously have insect-resistance, had a substantial loss of insect resistance. At present, Mudgo (comprising Bph1) has an average resistance level of 5.4, ASD7 (comprising Bph2) has an average resistance level of 8.89, Rathu Heenati (comprising Bph3) has an average resistance level of 4.61, Babawee (comprising Bph4) has an average resistance level of 8.14. While the insect-resistant variety BG1222 has an average resistance level of 1.07. By comparison, it can be found that the rice planthopper-sensitivity gene BGIOSGA015651 as disclosed by the present invention would be of great importance in rice breeding and in the improvement of planthopper resistance of rice.

The rice planthopper-sensitivity gene BGIOSGA015651 of the present invention can be used for rice breeding. The expression of the gene encoding this protein can be reduced or knocked out by molecular breeding methods or genetic engineering methods, resulting in that an insect-susceptible plant can have high insect-resistance. Thus, plants having high planthopper-resistance (*Nilaparvata lugens*- and *Sogatella furcifera*- resistance) can be bred. Therefore, the gene of the present invention and the encoded protein thereof can be used for the genetic improvement of plants.

The rice planthopper-sensitivity gene BGIOSGA015651 of the present invention is equally effective for *Nilaparvata lugens* and *Sogatella furcifera*, while its insect-resistance to *Laodelphax striatellus* is still under study. Since the brown planthopper has long-distance migration habits, it is currently the major pest to rice in China and many other Asian countries, but it cannot pass the winter in the rice area above North Latitude 25° C. *Sogatella furcifera* infection occurs in all rice regions nationwide (distributed in all rice regions from south to Hainan Island, north to Heilongjiang in China, and Southeast Asian countries). Therefore, the rice for breeding in this technology can be promoted in a wide range of rice growing areas, and has high economic values and outstanding ecological benefits.

DETAIL DESCRIPTION

Figure 1:
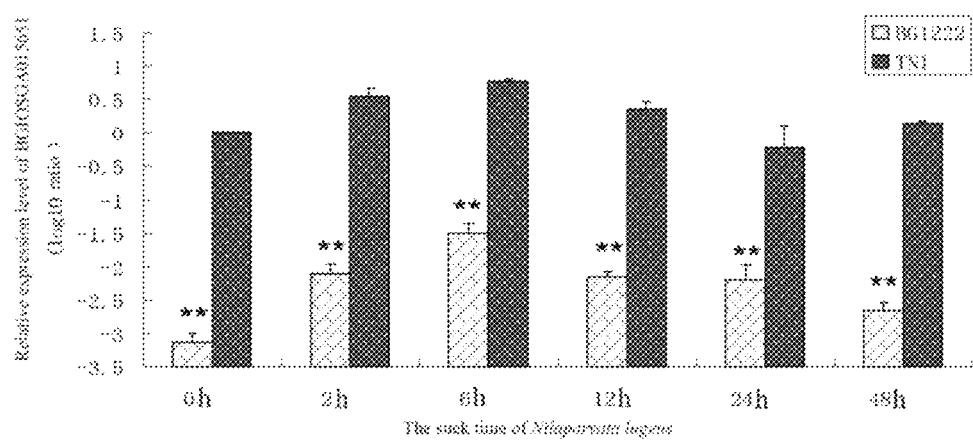
FIG. 1 is a graph showing the changes in the expression levels, over time, of BGIOSGA015651 in rice varieties BG1222 and TN1 after being sucked by the brown planthopper.

*Nilaparvata lugens* is a major pest that is harmful to rice production. In recent years, the brown planthopper damage has become more and more serious due to some reasons such as the variation of the biotypes of the brown planthopper and the development of drug-resistance, and the like. It has been proven by productive practices that the use of resistant varieties is most economical, safe and effective. According to "the standard seed box screening test", BG1222 was tested for insect-resistance level at the seedling stage for many years. BG1222 was found to have stable and high resistance to *Nilaparvata lugens*, and therefore has high utilization value in breeding. However, there is no domestic and foreign literature disclosing which key genes are related with the *Nilaparvata lugens*-resistance of BG1222. TN1 is internationally recognized as an insect-susceptible rice variety with no insect-resistant gene.

In addition to *Nilaparvata lugens*, other common species of planthoppers that are harmful to rice comprise *Sogatella furcifera* and *Laodelphax striatellus*. In southern China, it is mainly damaged by *Nilaparvata lugens* and *Sogatella furcifera*. In addition to directly sucking juice, *Sogatella furcifera* also acts as a main media for spreading rice viral diseases. BG1222 also has a certain level of resistance to *Sogatella furcifera*, which was confirmed by the inventors through the insect-resistance level test performed at seedling stage. This has not been reported in any literature.

The applicant of the present invention found a gene for regulating the planthopper-resistance of rice by studying on a rice variety BG1222 that has stable resistance to *Nilaparvata lugens* and *Sogatella furcifera*, and a rice variety TN1 that is susceptible to insects. This gene was named as BGIOSGA015651. It was found that the gene expression level of BGIOSGA015651 in the insect-resistant variety is significantly different from that of the insect-susceptible variety. The expression level of BGIOSGA015651 in the insect-resistant variety BG1222 is hundreds or more of times lower than that of the insect-susceptible rice variety TN1. The expression level of BGIOSGA015651 in BG1222 is much lower than that of TN1, regardless if it is sucked by *Nilaparvata lugens*. It is demonstrated by hybrid $F_2$ progeny verification that the expression level of BGIOSGA015651 is negatively related to the insect-resistance of rice (i.e., the lower the expression level, the stronger the insect resistance). In the progeny, the stronger the insect-resistance, the smaller the resistance score (Grade), and correspondingly the lower the expression level of BGIOSGA015651. The gene BGIOSGA015651 is knocked out by gene editing technology, such that the insect-susceptible rice variety TN1 can obtain insect-resistance as high as that of the rice variety BG1222.

Hereinafter the present invention will be further described with reference to specific Examples, but it would be appreciated that the present invention is not limited thereto.

Example 1. The Gene Expression Level of BGIOSGA015651 in the Insect-Resistant Variety is Significant Different from that of the Insect-Susceptible Variety I. Extraction of Total RNA in Rice 1) Grinding of Rice Samples The ultra-low temperature frozen rice samples were weighed and quickly transferred to a mortar precooled with liquid nitrogen. The tissue samples were ground with a pestle with continuously adding liquid nitrogen, until the samples were ground into powder. An appropriate amount, which matched the amount of sample homogenate, of RNAiso Plus could be added to the mortar. For fresh tissue samples, RNAiso Plus was added immediately and homogenized well. The homogenate was transferred to a centrifuge tube and allowed to stand at room temperature (15-30° C.) for 5 minutes. It was then centrifuged at 12,000 g for 5 minutes at 4° C. The supernatant was carefully pipetted to a new centrifuge tube.

2) Extraction of Total RNA

Chloroform (⅕ volume of RNAiso Plus) was added to the above homogenate lysate, and the centrifuge tube was tightly closed with a cap. The solution was mixed until it was emulsified to be milky white. Then, it was allowed to stand at room temperature for 5 minutes, followed by centrifuging at 12,000 g for 15 minutes at 4° C. The centrifuge tube was carefully removed from the centrifugal machine. At this moment, the homogenate was divided into three layers, i.e., a colorless supernatant (containing RNA), an intermediate white protein layer (mostly DNA), and a colored lower layer of organic phase. The supernatant was pipetted to a new centrifuge tube (not to pipet the white intermediate layer). A volume of isopropanol, which was 0.5-1 fold of RNAiso Plus, was added to the supernatant. Then, the tube was turned upside down and well mixed, and allowed to stand at room temperature for 10 minutes. It was then centrifuged at 12,000 g for 10 minutes at 4° C. Generally, RNA pellet occurred at the bottom of the tube after the centrifugation.

3) Cleaning of the RNA Pellet

The supernatant was carefully discarded, without affecting the pellet. A small amount of isopropanol could be remained. Then, a certain amount of 75% ethanol, which is equivalent to that of the RNAiso Plus, was added, and the wall of the centrifuge tube was washed by gently turning the tube upside down, followed by centrifuging at 7,500 g for 5 minutes at 4° C. The supernatant was carefully discarded, without affecting the pellet.

4) Dissolution of RNA

The tube cap was opened and the pellet was dried for a few minutes at room temperature. When the pellet was dried, an appropriate amount of RNase-free water was added to dissolve the pellet.

II. Removing of the Genome

The reaction solution was formulated by using DNase I of RNase-free according to the following system:

| | |
|---|---|
| RNA | 60 μl |
| DNase I | 20 μl |
| 10 x buffer | 20 μl |
| H$_2$O (RNase free) | 100 μl |
| Total volume | 200 μl |

Digestion was performed at 37° C. for 30 minutes, and inactivated at 65° C. for 10 minutes.

Then the experiment was performed following the steps of:

adding an equal volume of phenol, mixing well by turning upside down, then centrifuging at 10,000 rpm for 5 minutes, and pipetting the supernatant;

adding an equal volume of chloroform, mixing well by turning upside down, then centrifuging at 10,000 rpm for 10 minutes, and pipetting the supernatant;

adding an equal volume of isopropanol, mixing well and gently, and then standing at −20° C. for 15 minutes;

centrifuging at 10,000 g for 10 minutes at 4° C. to collect RNA pellet, and discarding the supernatant;

washing twice with 75% ethanol, and air drying in a super clean bench; and adding 10 μl DEPC water to dissolve the pellet.

III. Purity Detection and Electrophoresis Detection

Purity detection: 2 μl of RNA sample was taken and diluted 60 times, and OD value thereof was determined on a microspectrophotometer. It was showed that the ratio of OD 260/OD 280 was greater than 1.8, indicating that the resulted RNA was pure and had no protein contamination.

VI. Reverse Transcription

ART reaction solution was formulated according to the following (the formulation of reaction solution was performed on ice).

| | |
|---|---|
| RNA* | 2 μl |
| 5 x primeScript RT Master Mix (Perfect Real Time) | 2 μl |
| RNase-free ddH$_2$O | 6 μl |
| Total volume | 10 μl | indicates that the reaction system can be scaled up as required, and 500 ng of Total RNA can be used at most in 10 μl of the reaction system.

The above 10 μl of the reaction solution was reacted on a TaKaRa-TP600 PCR machine: 37° C. 15 minutes; 85° C. 5 seconds; maintained at 4° C., and then stored at −20° C. until use.

V. Quantification

The gene expression level of BGIOSGA015651 was analyzed using the following primer pairs, the base sequences thereof were as follows:

```
RE-f:
                                        (SEQ ID NO: 7)
TCCAGAGCAGGAAACAAGGAC,

RE-r:
                                        (SEQ ID NO: 8)
GCCTACGCCAGCACATGAAA.
```

Reaction system:

| | |
|---|---|
| cDNA template | 2 μl |
| Forward primer (RE-f) | 1 μl |
| Reverse primer (RE-r) | 1 μl |
| SYBR Premix Ex TaqII (Tli RNaseH Plus) (2 X) | 12.5 μl |
| dH$_2$O | 8.5 μl |
| Total volume | 25 μl |

Real Time PCR reactions

Real Time PCR reactions were performed on a CFX96 Real-Time (Bio-Rad) PCR machine: 95° C. 30 seconds; 95° C. 5 seconds, 60° C. 30 seconds, 40 cycles. Analysis of the melting curve: temperature 60° C.-95° C.

The results are shown in FIG. 1.

FIG. 1 shows the changes in the expression levels, over time, of BGIOSGA015651 in rice varieties BG1222 and TN1 after being sucked by *Nilaparvata lugens*.

It demonstrates by the results as shown in FIG. 1 that the gene expression levels of BGIOSGA015651 in the insect-resistant variety is significantly differently from that of the insect-susceptible variety. The expression levels of BGIOSGA015651 in the insect-resistant variety BG1222 is hundreds of times, or even thousands or more of times lower than that of the insect-susceptible rice variety TN1. The expression levels of BGIOSGA015651 in BG1222 are much lower than that of TN1, regardless if it is sucked by *Nilaparvata lugens* (sucking for different hours).

Example 2. Cloning of Gene BGIOSGA015651 and Analysis of the Peptide Thereof

The genes BGIOSGA015651 of the insect-resistant variety BG1222 and the insect-susceptible variety TN1 were cloned, sequenced and analyzed, respectively.

The nucleotide sequence of gene BGIOSGA015651 in the insect-resistant variety BG1222 was as shown by SEQ ID NO: 1 (including exons and introns), and the nucleotide sequence of gene BGIOSGA015651 in the insect-susceptible variety TN1 was as shown by SEQ. ID NO: 2 (including exons and introns). There were several different nucleotides between the two nucleotide sequences.

The cDNA sequence of gene BGIOSGA015651 in the insect-resistant variety BG1222 was as shown by SEQ ID NO: 3, while the cDNA sequence of gene BGIOSGA015651 in the insect-susceptible variety TN1 was as shown by SEQ. ID NO: 4.

The protein encoded by gene BGIOSGA015651 in the insect-resistant variety BG1222 was as shown by SEQ ID NO: 5, while the protein encoded by gene BGIOSGA015651 in the insect-susceptible variety TN1 was as shown by SEQ. ID NO: 6. There were 16 different amino acids between the two proteins.

Example 3. Hybrid $F_2$ Progeny Between the Insect-Resistant Variety and the Insect-Susceptible Variety A population of $F_2$ progeny was established by hybridizing BG1222 with TN1. The samples of $F_2$ progeny population was 512 (i.e. n=512), from which sixty plants with different resistance scores were selected for detection. The expression levels of BGIOSGA015651 were detected for the $F_2$ progeny plants having phenotypes of different resistance-levels, so as to determine the correlation between the expression level of BGIOSGA015651 and the insect-resistant phenotype of rice.

Figure 2:
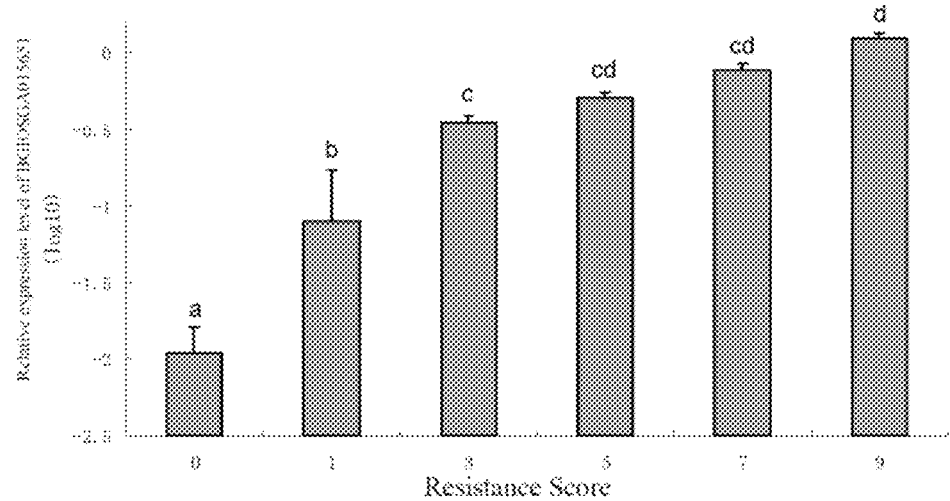
FIG. 2 is a graph showing, in hybrid $F_2$ progeny, the relationship between the expression level of BGIOSGA015651 and the insect-resistance score of rice.

The results are shown in FIG. 2.

FIG. 2 is a graph showing, in the hybrid $F_2$ progeny, the relationship between the expression level of BGIOSGA015651 and the insect-resistance score of rice.

The bar graph of FIG. 2 shows the relationship between the expression level of BGIOSGA015651 and the insect-resistance scores of plants representing hybrid F2 progeny plants. The horizontal axis shows the insect-resistance scores (i.e. 0, 1, 3, 5, 7 and 9), and the vertical axis shows the expression level (in log10) of BGIOSGA015651, wherein a shorter bar on the graph of FIG. 2 indicates a lower expression level of BGIOSGA015651. According to FIG. 2, it can be seen that, with the decrease of the expression level of BGIOSGA015651, the insect-resistance score is also gradually reduced (i.e. from right to left), and the shortest bar has the lowest insect-resistance score (0) and the lowest expression level of BGIOSGA015651. The letters (i.e. "a", "b", "c", "cd", and "d") above the bars indicate the statistically relationship between the data represented by each bar.

It demonstrates by the results as shown in FIG. 2 that, in the hybrid $F_2$ progeny, the expression level of gene BGIOSGA015651 is negatively related to the insect-resistance of rice (the lower the expression level, the stronger the insect-resistance). It shows that the stronger the insect-resistance in the progeny, the smaller the resistance score (Grade), and correspondingly the lower the expression level of BGIOSGA015651.

Example 4. Gene Knockout Experiment

Gene BGIOSGA015651 was knocked out by gene editing technology in the gene knockout experiment, such that the insect-susceptible rice variety TN1 can obtain insect resistance as high as that of the rice variety BG1222.

I. Construction of a Gene-Knockout Vector in Rice

A fragment located at the front end of the cDNA sequence of gene BGIOSGA015651 was selected as a target sequence, and a gRNA (guide RNA) sequence was designed and synthesized (the sequences was shown as follows, but the target sequence and the corresponding gRNA sequence were not limited to them). The gRNA sequence was recombined into apBWA(V)H vector (Wuhan BioRun Co., Ltd.) containing a hygromycin-resistance tag. The vector system was engineered by using the CRISPR/Cas9 genome, and one base in the target sequence was mutated (i.e., deleting or adding one base in the target sequence). The cDNA sequence of gene BGIOSGA015651 was subjected to frame shift mutation, such that the expressed protein thereof was not the same as the original amino acid product, thereby achieving the purpose of knocking out gene BGIOSGA015651.

```
gRNA sequence:
                              (SEQ ID NO: 9)
5'-CATCTCTCAGTGCACGGCT-3';

Target sequence:
                              (SEQ ID NO: 10)
5'-ACATCTCTCAGTGCACGGCTGGG-3'.
```

II. Obtaining Rice Seedlings with Gene Knockout by Genetic Transformation

Inducing callus from a mature embryo of the insect-susceptible rice TN1: Cultured Agrobacterium (EHA105) solution was placed in a centrifuge tube and centrifuged. The supernatant was pipetted to prepare Agrobacterium suspension. A callus having a certain size was picked out and placed in the Agrobacterium suspension for infection. Then the callus was placed on the co-culture medium.

2) Screening: The callus was removed and dried. The dried callus was transferred to screening medium for a first screening. An initial callus comprising resistant callus was transferred to new medium for a second screening.

3) Induced differentiation and rooting of the resistant callus: The resistant callus was picked out, transferred to a culture dish containing differentiation medium. Then, the culture dish was sealed with sealing film, and placed in a constant temperature culture chamber to make the resistant callus to differentiate into seedlings. When the size of the seedlings was about 1 cm, the seedlings were transferred to rooting medium for culturing strong seedlings.

4) PCR detection of hygromycin (Hyg) resistant gene: A conventional PCR amplification method was used to determine whether the rice seedling comprised this gene by using hygromycin resistant gene-specific primers. If the rice seedling comprised this gene, it would be a transformation positive seedling.

Resistant gene specific primers:

```
Hyg-f:
                              (SEQ ID NO: 11)
5'-ACGGTGTCGTCCATCACAGTTTGCC-3';

Hyg-r:
                              (SEQ ID NO: 12)
5'-TTCCGGAAGTGCTTGACATTGGGA-3'.
```

5) Gene knockout detection of positive seedlings: PCR reaction was performed by using the detection primers designed in the vicinity of the target. The PCR product was then sequenced to detect gene knockout (whether or not a knockout homozygous seedling was obtained). Homozygous seedlings, in which gene BGIOSGA015651 of the insect-susceptible rice TN1 were successfully knocked out, were obtained.

III. Identification of Insect-Resistance of Rice Seedlings with Gene Knockout

Homozygous seedlings, in which gene BGIOSGA015651 of the insect-susceptible rice TN1was successfully knocked out, were identified for insect resistance at seedling stage.

The identified results were as follows: the mortality rate of the insect-susceptible receptor variety TN1 was 100%; the mortality rate of homozygous seedlings, in which gene BGIOSGA015651 was knocked out, was 0% and the resistance level thereof was 0-1 (i.e., high resistance level).

It is verified that the expression level of gene BGIOSGA015651 is negatively related to the insect resistance of rice (the lower the expression level, the stronger the insect resistance). Thus, gene BGIOSGA015651 is an important gene related to rice planthopper resistance.

Example 5. Comparison Between Insect-Resistance Effect of Gene BGIOSGA015651 and that of Existing *Nilaparvata lugens*-Resistant Genes In the present invention, after gene BGIOSGA015651 was knocked out from the insect-susceptible rice variety TN1 (having an original resistance level of 9), the resistance level thereof was significantly increased to level 0-1, which was equivalent to or better than that of insect-resistant variety BG1222 (having a resistance level of 1.07).

The applicants found that the varieties, which previously have insect-resistance, had a substantial loss of insect resistance through rice seedling identification. At present, Mudgo (comprising Bph1) has an average resistance level of 5.4, ASD7 (comprising Bph2) has an average resistance level of 8.89, Rathu Heenati (comprising Bph3) has an average resistance level of 4.61, Babavee (comprising Bph4) has an average resistance level of 8.14, while the insect resistant variety BG1222 has an average resistance level of 1.07.

By comparison, it can be found that the rice planthopper sensitivity gene BGIOSGA015651 of the present invention has a great prospect in rice breeding. With molecular breeding methods or genetic engineering methods, it can change an insect-susceptible plant to one having high insect-resistance by reducing or knocking out the expression of the protein-encoding gene, thereby obtaining highly planthopper resistant (e.g. *Nilaparvata lugens* resistant and *Sogatella furcifera* resistant) rice varieties.

Example 6. Resistance Against *Sogatella furcifera* of BGIOSGA015651

In the present invention, after gene BGIOSGA015651 was knocked out from the insect-susceptible rice variety TN1 (having an original resistance level of level 9), the resistance level thereof against *Sogatella furcifera* was identified at the seedling stage.

The results were as follows: the mortality rate of the insect-susceptible receptor variety TN1 was 100%; the mortality rate of homozygous seedlings, in which gene BGIOSGA015651 was knocked out, was 0% and the resistance level thereof was 0-1 (i.e., high resistance level).

Therefore, the rice planthopper-sensitivity gene BGIOSGA015651 of the present invention is also effective for breeding of seedlings having resistance against *Sogatella furcifera*.

The above examples are preferred embodiments of the present invention, and the embodiments of the present invention are not limited to these examples. Any other alterations, modifications, substitutions, combinations, and simplification can be made without departing from the spirit and principle of the present invention, and all belong to equivalent alternations and fall in the protection scope of the present invention.

What is claimed is:

1. A method for improving the insect resistance of a rice plant, comprising:
   (A) providing a rice plant comprising insect-resistant variety of insect-sensitivity gene BGIOSGA015651, wherein the insect-resistant variety has the sequence of SEQ ID NO: 1 or SEQ ID NO: 3;
   cross breeding the rice plant comprising SEQ ID NO: 1 or SEQ ID NO: 3 with a rice plant comprising insect-sensitivity gene BGIOSGA015651 of SEQ ID NO: 2 or SEQ ID NO: 4 to produce a progeny rice plant; and
   Obtaining a progeny rice plant comprising SEQ ID NO: 1 or SEQ ID NO: 3 and that is insect resistant, or
   (B) Reducing or abolishing the expression of SEQ ID NO: 2 or SEQ ID NO: 4 in a rice plant by producing a non-natural mutation into SEQ ID NO: 2 or SEQ ID NO: 4 by genetic engineering or by breeding.

2. The method according to claim 1, wherein the insect resistance of the rice plant is resistance to planthoppers.

3. The method according to claim 1, wherein the insect resistance is resistance to insects selected from the group consisting of *Nilaparvata lugens, Sogatella furcifera*, and *Laodelphax striatellus*.

4. A rice seed, tissue, plant part, or progeny comprising the non-natural mutation of claim 1, wherein the mutation results in reduced or abolished expression of SEQ ID NO: 2 or SEQ ID NO: 4, and/or reduced or abolished level or activity of a protein encoded by insect sensitivity gene BGIOSGA015651 of SEQ ID NO: 2 or SEQ ID NO: 4, wherein the rice seed, tissue, plant part, or progeny has increased resistance to one or more insects as compared to rice seed, tissue, plant part, or progeny that does not comprise the non-natural mutation in SEQ ID NO: 2 or SEQ ID NO: 4.

5. The rice seed, tissue, plant part, or progeny according to claim 4, wherein the non-natural mutation is produced by genetic engineering.

6. The rice seed, tissue, plant part, or progeny according to claim 4, wherein the non-natural mutation is produced by breeding.

7. The rice seed, tissue, plant part, or progeny according to claim 5, wherein the genetic engineering method comprises RNA interference or gene editing.

8. The rice seed, tissue, plant part, or progeny according to claim 4, wherein the insect resistance is resistance to planthoppers.

9. The rice seed, tissue, plant part, or progeny according to claim 4, wherein the insect resistance is resistance to insects selected from the group consisting of *Nilaparvata lugens, Sogatella furcifera* and *Laodelphax striatellus*.

10. The rice seed, tissue, plant part, or progeny according to claim 9, wherein the insect resistance is resistance to insects selected from the group consisting of *Nilaparvata lugens* and *Sogatellafircifera*.

\* \* \* \* \*

SEQUENCE LISTING

```
<160> NUMBER OF SEQ ID NOS: 12

<210> SEQ ID NO 1
<211> LENGTH: 2542
<212> TYPE: DNA
<213> ORGANISM: Oryza.sativa L.

<400> SEQUENCE: 1
atggcctgcc tgcagctgca ggttcttctc ctcctcgcct gcctgctgct tgatgctcct     60
catcttagta gtgctgcagc cacagttcca acaccaccct tctccttcaa cttcgacttc    120
tccaacatgt ccacatacaa gccggatgac ttgaaatttg agggcaacgc gactgtgcac    180
ggcagcttcg tcgacctcac ctgcaacgca tacgggctgg acatctctca gtgcacggct    240
gggcggatgt cgtacagtca cccggtgccc ttctacgacc aaaccaccaa ggaggttgcc    300
agcttctcca cacagttcac cttcaagatt attgtaccaa gatttaacaa cgacaaggag    360
aagggagatg gtatggcttt cttccttgca cgttacccat caagaatgcc tccagattca    420
ggcggcggca gccttggtct catcaccaac gataactatt ctagcattgg cccggaccag    480
ttcgtatccg tcgagtttga tacgtacaac aacacctggg agcagcctaa gcagactggt    540
gaccatatgg gcatcaacat caacacagtc actttttcga ctaacacaac aagtgtatcc    600
agcttcagcc cgaatgagag catgatgaag gcgtccatca cctttgacag caagacctcg    660
atgctggtcg cctctctgca gtataccggt aattattcta actatgcccc tgttaacgtc    720
agtgcgaaac tcccagatcc tacgaccttg ctcccgtcgg aggtggcagt gggattttct    780
gcaggcaccg gggtagcctt cgagctccat caaatacact catggtcttt caactcaact    840
attgctgccc cggtaaaaaa aggtatatat gcagttacta catctcttga attgattgtt    900
ggattaatgc attgtactcg ttggacgtac ttctgacgca gcaattgaca cgttagtagt    960
ttgtattttt tttgaatgaa tttgtaatgc agcaattgac accgatctgc cgtaacatcg   1020
atgcagatca caagaaagcc attgccgtag gggtctcaat tggaggaggt ctcatattgg   1080
tgctcctggt gtggtctatt ctctcatggt ggaagtggag aaaaacaaac cgtgaatttg   1140
acaagggaac tcgtggggct tgtcggttca actaccacca cttggctgct gcaacaaacc   1200
atttttcaat ggataatagg attggagcag gtgcgttcgg tgaagtacac aaaggtttct   1260
tgacacaatt gggccgtgaa gtggctgtta agaagatctt gagggaatcc agagcaggaa   1320
acaaggactt ttttgacgaa gtccagacca tcagtagagc aaagcagaag aatcttgttg   1380
aacttcttgg ttggggaatg aagggcagct cgatcattat tgatttcatg tgctggcgta   1440
ggcagaagaa catcgacctt ttcctggtat atgaatttgt ggataacggc aacctacata   1500
```

```
tgcacctgta tgagaaggag gccctgctgt catggagaat aaggtacata ctgcgagctg    1560
agcaatataa tttatattca aattttaaga acctagctag gtattattat attactaccg    1620
cacacataac cccaaaaatt attgtctaat aatgttttac aaaactccac catgtccatg    1680
ttgagcataa ttttctaaa aataaaatat agattgtata tgaaaattgt aattactgat    1740
ttcttgacta aggttgatag tttaactttt cactgcttta aaaaaattat tttagatatg    1800
tttaaattaa atgacatttc aataatacct atatatgggt tttctgccac atagacccta    1860
aaacatgttg tttcctggaa gtaactattt tgaatatgga agtttgaaaa aacgagctag    1920
taatgttgac aatcattatg tacgttcctc ggaacaagaa aatgattatg catgcaaatg    1980
ttgtcttttc aggtataaaa tagtgaaggg cattatcagc gctcttgttt accttcacca    2040
tgatagacat ccatacattc ttcacaggga tatcaaaccg agcaacatac tcttggacaa    2100
aaatttcaat gctagattag cagatttcgg gctgtcgaga actgctgaca acggaacaat    2160
acaatcgtca atggtagtag gaacagcaaa ctacttggat ccagagtgca tgaagacggg    2220
aaagttcaat cgtagctctg atgtcttcag cttcgggctc gttctgctag agattgcttg    2280
caagaaagac gaaaatagct atgcacaagt ctgggaaaga tacatcgaca aaactctgat    2340
gcatgctgct gacgataggt tacagggttc gttcgacaag aggcagatgg agcgtttgat    2400
cgtcttgggg ctgtggtgtt gtcagcccaa tattgagatg cgacctacga tggagcaagc    2460
aatggatttc ctggagagtg atgggccgtt gcctaaactg gccaaacccg aaattacctc    2520
ctcaagtgcg ccaagcaatt ga                                            2542

<210> SEQ ID NO 2
<211> LENGTH: 2542
<212> TYPE: DNA
<213> ORGANISM: Oryza.sativa L.

<400> SEQUENCE: 2
atggcctgcc tgcagctgca ggttcttctc ctcctcgcct gctgctgct tgatgctcat     60 catcttagta gtgctgcagc cacagttcca acaccaccct tctccttcaa cttcgacttc    120
tccaacatgt ccacatacaa gccggatgac ttgagatttg agggcaacgc gactgtgcac    180
ggcagcttcg tcgacctcac ctgcaacgca tatgggctgg acatctctca gtgcacggct    240
gggcggatgt cgtacaatca cccggtgccc ttctacgacc aaaccaccaa ggaggttgcc    300
agcttctcca cacagttcac cttcaagatt attgtaccaa gatttaacaa cgacaaggag    360
aagggagatg gtatggcttt cttccttgca cgttacccat caagaatgcc tccagattca    420
ggcggcggca gccttggtct catcaccaac aacaactata gtagctttgg cccggaccag    480
ttcgtatccg tcgagtttga tacgtacaac aacacctggg agcagcctaa gcagactggt    540
gaccatatgg gcatcaacat caacacagtc acttttcga ctaacacaac aagtgtatcc    600
agcttcagcc cgaatgagag catgatgaag gcgtccatca cctttgacag caagacctcg    660
atgctggtcg cctctctgca gtataccggt aattattcta acattgcccc tgttaacgtc    720
agtgcgaaac tcccagatcc tacgaccttg ctcccgtcgg aggtggcagt gggattttct    780
gcagccaccg gggcagcctt cgagctccat caaatacact catggtcttt caactcaact    840
attgctgccc cggtaaaaaa aggtatatat gcagttacta catctcttga attgatcgtt    900
ggattaatgc attgtactcg ttggacgtac ttctgacgca gcaattgaca ccttagtagt    960
ttgtattttt tttgaatgaa tttgtaatgc agcaattgac accgatctgc cgtaacatcg   1020
```

```
atgcagatca caagaaagcc attgccgtag gggtctcaat tggaggaggt ctcatattgg    1080
tgctcctggt gtggtctatt ctctcatggt ggaagtggag aaaaacaaac cgtgaatttg    1140
acaagggaac tcgtggggct tgtcggttca actaccacca cttggctgct gcaacaaacc    1200
attttttcaat ggataatagg attggagcag gtgcgttcgg tgaagtacac aaaggtttct    1260
tgacacaatt gggccgtgaa gtggctgtta agaagatctt gagggaatcc agagcaggaa    1320
acaaggactt ttttgacgaa gtccagacca tcagtagagc aaagcagaag aatcttgttg    1380
aacttcttgg ttggggaatg aagggcagct cgaacattat tgatttcatg tgctggcgta    1440
ggcagaagaa caccgacctt ttcctggtat atgaatttgt ggataacggc aacctacata    1500
tgcacctgta tgagaaggag gccctgctgt catggagaat aaggtacata ctgcgagctg    1560
agcaatataa tttatattca aattttaaga acctagctag gtattattat attactaccg    1620
cacacataac cccaaaaatt attgtctaat aatgttttac aaaactccac catgtccatg    1680
ttgagcataa ttttttctaaa aataaaatat agattgtata tgaaaattgt aattactgat    1740
ttcttgacta aggttgatag tttaactttt cactgcttta aaaaaattat tttagatatg    1800
tttaaattaa atgacatttc aataatacct atatatgggt tttctgccac atagacccta    1860
aaacatgttg tttcctggaa gtaactattt tgaatatgga agtttgaaaa aacgagctag    1920
taatgttgac aatcattatg tacgttcctc ggaacaagaa aatgattatg catgcaaatg    1980
ttgtcttttc aggtataaaa tagtgaaggg cattatcagc gctcttgttt accttcacca    2040
tgatagacat ccatacattc ttcacaggga tatcaaaccg agcaacatac tcttggacaa    2100
aaatttcaat gctagattag cagatttcgg gctgtcgaga actgccgaca atggaacaat    2160
acaatcgtca atggttgtag gaacggaaaa ttacttggat ccagagtgca ggaagacggg    2220
aaagttcaac cgtagctcag atgtcttcag cttcgggctc gttctgctag agattgcttg    2280
caagaaagac gagaatagct atgcacaagt ctgggaaagg tacatcgaca aaactctgat    2340
gcaggctgct gacgataggt tacaaggtgc gttcgataag aggcagatgg agcgtgtgat    2400
cgtcttgggg ctgtggtgtt gtcagcctaa tattgagatg cgacctacga tggagaaagc    2460
aatggatttc ctggagagtg atgggccgtt gcctaaactg gccaaacccg aaattacctc    2520
ctcaagtgcg ccaagcaatt ga                                              2542

<210> SEQ ID NO 3
<211> LENGTH: 1953
<212> TYPE: DNA
<213> ORGANISM: Oryza.sativa L.

<400> SEQUENCE: 3
atggcctgcc tgcagctgca ggttcttctc ctcctcgcct gctgctgct tgatgctcct     60
catcttagta gtgctgcagc cacagttcca acaccaccct tctccttcaa cttcgacttc    120
tccaacatgt ccatacacaa gccggatgac ttgaaatttg agggcaacgc gactgtgcac    180
ggcagcttcg tcgacctcac ctgcaacgca tacgggctgg acatctctca gtgcacggct    240
gggcggatgt cgtacagtca cccggtgccc ttctacgacc aaaccaccaa ggaggttgcc    300
agcttctcca cacagttcac cttcaagatt attgtaccaa gatttaacaa cgacaaggag    360
aagggagatg gtatggcttt cttccttgca cgttacccat caagaatgcc tccagattca    420
ggcggcggca gccttggtct catcaccaac gataactatt ctagcattgg cccggaccag    480
ttcgtatccg tcgagtttga tacgtacaac aacacctggg agcagcctaa gcagactggt    540
gaccatatgg gcatcaacat caacacagtc acttttcga ctaacacaac aagtgtatcc    600
```

| | | | | |
|---|---|---|---|---|
| agcttcagcc | cgaatgagag | catgatgaag | gcgtccatca | cctttgacag | caagacctcg | 660 |
| atgctggtcg | cctctctgca | gtataccggt | aattattcta | actatgcccc | tgttaacgtc | 720 |
| agtgcgaaac | tcccagatcc | tacgaccttg | ctcccgtcgg | aggtggcagt | gggattttct | 780 |
| gcaggcaccg | gggtagcctt | cgagctccat | caaatacact | catggtcttt | caactcaact | 840 |
| attgctgccc | cgcaattgac | accgatctgc | cgtaacatcg | atgcagatca | caagaaagcc | 900 |
| attgccgtag | gggtctcaat | tggaggaggt | ctcatattgg | tgctcctggt | gtggtctatt | 960 |
| ctctcatggt | ggaagtggag | aaaaacaaac | cgtgaatttg | acaagggaac | tcgtggggct | 1020 |
| tgtcggttca | actaccacca | cttggctgct | gcaacaaacc | attttcaat | ggataatagg | 1080 |
| attggagcag | gtgcgttcgg | tgaagtacac | aaaggtttct | tgacacaatt | gggccgtgaa | 1140 |
| gtggctgtta | agaagatctt | gagggaatcc | agagcaggaa | acaaggactt | ttttgacgaa | 1200 |
| gtccagacca | tcagtagagc | aaagcagaag | aatcttgttg | aacttcttgg | ttggggaatg | 1260 |
| aagggcagct | cgatcattat | tgatttcatg | tgctggcgta | ggcagaagaa | catcgacctt | 1320 |
| ttcctggtat | atgaatttgt | ggataacggc | aacctacata | tgcacctgta | tgagaaggag | 1380 |
| gccctgctgt | catggagaat | aaggtataaa | atagtgaagg | gcattatcag | cgctcttgtt | 1440 |
| taccttcacc | atgatagaca | tccatacatt | cttcacaggg | atatcaaacc | gagcaacata | 1500 |
| ctcttggaca | aaaatttcaa | tgctagatta | gcagatttcg | ggctgtcgag | aactgctgac | 1560 |
| aacggaacaa | tacaatcgtc | aatggtagta | ggaacagcaa | actacttgga | tccagagtgc | 1620 |
| atgaagacgg | gaaagttcaa | tcgtagctct | gatgtcttca | gcttcgggct | cgttctgcta | 1680 |
| gagattgctt | gcaagaaaga | cgaaaatagc | tatgcacaag | tctgggaaag | atacatcgac | 1740 |
| aaaactctga | tgcatgctgc | tgacgatagg | ttacagggtt | cgttcgacaa | gaggcagatg | 1800 |
| gagcgtttga | tcgtcttggg | gctgtggtgt | tgtcagccca | atattgagat | gcgacctacg | 1860 |
| atggagcaag | caatggattt | cctggagagt | gatgggccgt | tgcctaaact | ggccaaaccc | 1920 |
| gaaattacct | cctcaagtgc | gccaagcaat | tga | | | 1953 |

<210> SEQ ID NO 4
<211> LENGTH: 1953
<212> TYPE: DNA
<213> ORGANISM: Oryza.sativa L.

<400> SEQUENCE: 4

| | | | | |
|---|---|---|---|---|
| atggcctgcc | tgcagctgca | ggttcttctc | ctcctcgcct | gcctgctgct | tgatgctcat | 60 |
| catcttagta | gtgctgcagc | cacagttcca | acaccaccct | tctccttcaa | cttcgacttc | 120 |
| tccaacatgt | ccacatacaa | gccggatgac | ttgagatttg | agggcaacgc | gactgtgcac | 180 |
| ggcagcttcg | tcgacctcac | ctgcaacgca | tatgggctgg | acatctctca | gtgcacggct | 240 |
| gggcggatgt | cgtacaatca | cccggtgccc | ttctacgacc | aaaccaccaa | ggaggttgcc | 300 |
| agcttctcca | cacagttcac | cttcaagatt | attgtaccaa | gatttaacaa | cgacaaggag | 360 |
| aagggagatg | gtatggcttt | cttccttgca | cgttacccat | caagaatgcc | tccagattca | 420 |
| ggcggcggca | gccttggtct | catcaccaac | aacaactata | gtagctttgg | cccggaccag | 480 |
| ttcgtatccg | tcgagtttga | tacgtacaac | aacacctggg | agcagcctaa | gcagactggt | 540 |
| gaccatatgg | gcatcaacat | caacacagtc | acttttttcga | ctaacacaac | aagtgtatcc | 600 |
| agcttcagcc | cgaatgagag | catgatgaag | gcgtccatca | cctttgacag | caagacctcg | 660 |
| atgctggtcg | cctctctgca | gtataccggt | aattattcta | acattgcccc | tgttaacgtc | 720 |

```
agtgcgaaac tcccagatcc tacgaccttg ctcccgtcgg aggtggcagt gggattttct    780
gcagccaccg gggcagcctt cgagctccat caaatacact catggtcttt caactcaact    840
attgctgccc cgcaattgac accgatctgc cgtaacatcg atgcagatca caagaaagcc    900
attgccgtag gggtctcaat tggaggaggt ctcatattgg tgctcctggt gtggtctatt    960
ctctcatggt ggaagtggag aaaaacaaac cgtgaatttg acaagggaac tcgtggggct   1020
tgtcggttca actaccacca cttggctgct gcaacaaacc attttcaat ggataatagg    1080 attggagcag gtgcgttcgg tgaagtacac aaaggtttct tgacacaatt gggccgtgaa   1140
gtggctgtta agaagatctt gagggaatcc agagcaggaa acaaggactt ttttgacgaa   1200
gtccagacca tcagtagagc aaagcagaag aatcttgttg aacttcttgg ttggggaatg   1260
aagggcagct cgaacattat tgatttcatg tgctggcgta ggcagaagaa caccgacctt   1320
ttcctggtat atgaatttgt ggataacggc aacctacata tgcacctgta tgagaaggag   1380
gccctgctgt catggagaat aaggtataaa atagtgaagg cattatcag cgctcttgtt    1440 taccttcacc atgatagaca tccatacatt cttcacaggg atatcaaacc gagcaacata   1500
ctcttggaca aaaatttcaa tgctagatta gcagatttcg ggctgtcgag aactgccgac   1560
aatggaacaa tacaatcgtc aatggttgta ggaacgaaaa attacttgga tccagagtgc   1620
aggaagacgg gaaagttcaa ccgtagctca gatgtcttca gcttcgggct cgttctgcta   1680
gagattgctt gcaagaaaga cgagaatagc tatgcacaag tctgggaaag gtacatcgac   1740
aaaactctga tgcaggctgc tgacgatagg ttacaaggtg cgttcgataa gaggcagatg   1800
gagcgtgtga tcgtcttggg gctgtggtgt tgtcagccta atattgagat gcgacctacg   1860
atggagaaag caatggattt cctggagagt gatgggccgt tgcctaaact ggccaaaccc   1920
gaaattacct cctcaagtgc gccaagcaat tga                                1953

<210> SEQ ID NO 5
<211> LENGTH: 650
<212> TYPE: PRT
<213> ORGANISM: Oryza.sativa L.

<400> SEQUENCE: 5

Met Ala Cys Leu Gln Leu Gln Val Leu Leu Leu Ala Cys Leu Leu
1               5                   10                  15

Leu Asp Ala Pro His Leu Ser Ser Ala Ala Thr Val Pro Thr Pro
                20                  25                  30

Pro Phe Ser Phe Asn Phe Asp Phe Ser Asn Met Ser Thr Tyr Lys Pro
            35                  40                  45

Asp Asp Leu Lys Phe Glu Gly Asn Ala Thr Val His Gly Ser Phe Val
        50                  55                  60

Asp Leu Thr Cys Asn Ala Tyr Gly Leu Asp Ile Ser Gln Cys Thr Ala
65                  70                  75                  80

Gly Arg Met Ser Tyr Ser His Pro Val Pro Phe Tyr Asp Gln Thr Thr
                85                  90                  95

Lys Glu Val Ala Ser Phe Ser Thr Gln Phe Thr Phe Lys Ile Ile Val
                100                 105                 110

Pro Arg Phe Asn Asn Asp Lys Glu Lys Gly Asp Gly Met Ala Phe Phe
            115                 120                 125

Leu Ala Arg Tyr Pro Ser Arg Met Pro Pro Asp Ser Gly Gly Gly Ser
        130                 135                 140

Leu Gly Leu Ile Thr Asn Asp Asn Tyr Ser Ser Ile Gly Pro Asp Gln
145                 150                 155                 160
```

```
Phe Val Ser Val Glu Phe Asp Thr Tyr Asn Asn Thr Trp Glu Gln Pro
                165                 170                 175
Lys Gln Thr Gly Asp His Met Gly Ile Asn Ile Asn Thr Val Thr Phe
            180                 185                 190
Ser Thr Asn Thr Thr Ser Val Ser Ser Phe Ser Pro Asn Glu Ser Met
            195                 200                 205
Met Lys Ala Ser Ile Thr Phe Asp Ser Lys Thr Ser Met Leu Val Ala
        210                 215                 220
Ser Leu Gln Tyr Thr Gly Asn Tyr Ser Asn Tyr Ala Pro Val Asn Val
225                 230                 235                 240
Ser Ala Lys Leu Pro Asp Pro Thr Leu Leu Pro Ser Glu Val Ala
                245                 250                 255
Val Gly Phe Ser Ala Gly Thr Gly Val Ala Phe Glu Leu His Gln Ile
                260                 265                 270
His Ser Trp Ser Phe Asn Ser Thr Ile Ala Ala Pro Gln Leu Thr Pro
            275                 280                 285
Ile Cys Arg Asn Ile Asp Ala Asp His Lys Lys Ala Ile Ala Val Gly
        290                 295                 300
Val Ser Ile Gly Gly Leu Ile Leu Val Leu Leu Val Trp Ser Ile
305                 310                 315                 320
Leu Ser Trp Trp Lys Trp Arg Lys Thr Asn Arg Glu Phe Asp Lys Gly
                325                 330                 335
Thr Arg Gly Ala Cys Arg Phe Asn Tyr His His Leu Ala Ala Ala Thr
                340                 345                 350
Asn His Phe Ser Met Asp Asn Arg Ile Gly Ala Gly Ala Phe Gly Glu
            355                 360                 365
Val His Lys Gly Phe Leu Thr Gln Leu Gly Arg Glu Val Ala Val Lys
        370                 375                 380
Lys Ile Leu Arg Glu Ser Arg Ala Gly Asn Lys Asp Phe Phe Asp Glu
385                 390                 395                 400
Val Gln Thr Ile Ser Arg Ala Lys Gln Lys Asn Leu Val Glu Leu Leu
                405                 410                 415
Gly Trp Gly Met Lys Gly Ser Ser Ile Ile Ile Asp Phe Met Cys Trp
                420                 425                 430
Arg Arg Gln Lys Asn Ile Asp Leu Phe Leu Val Tyr Glu Phe Val Asp
            435                 440                 445
Asn Gly Asn Leu His Met His Leu Tyr Glu Lys Glu Ala Leu Leu Ser
        450                 455                 460
Trp Arg Ile Arg Tyr Lys Ile Val Lys Gly Ile Ile Ser Ala Leu Val
465                 470                 475                 480
Tyr Leu His His Asp Arg His Pro Tyr Ile Leu His Arg Asp Ile Lys
                485                 490                 495
Pro Ser Asn Ile Leu Leu Asp Lys Asn Phe Asn Ala Arg Leu Ala Asp
                500                 505                 510
Phe Gly Leu Ser Arg Thr Ala Asp Asn Gly Thr Ile Gln Ser Ser Met
            515                 520                 525
Val Val Gly Thr Ala Asn Tyr Leu Asp Pro Glu Cys Met Lys Thr Gly
        530                 535                 540
Lys Phe Asn Arg Ser Ser Asp Val Phe Ser Phe Gly Leu Val Leu Leu
545                 550                 555                 560
Glu Ile Ala Cys Lys Lys Asp Glu Asn Ser Tyr Ala Gln Val Trp Glu
                565                 570                 575
```

```
Arg Tyr Ile Asp Lys Thr Leu Met His Ala Ala Asp Arg Leu Gln
                580                 585                 590
Gly Ser Phe Asp Lys Arg Gln Met Glu Arg Leu Ile Val Leu Gly Leu
        595                 600                 605
Trp Cys Cys Gln Pro Asn Ile Glu Met Arg Pro Thr Met Glu Gln Ala
        610                 615                 620
Met Asp Phe Leu Glu Ser Asp Gly Pro Leu Pro Lys Leu Ala Lys Pro
625                 630                 635                 640
Glu Ile Thr Ser Ser Ser Ala Pro Ser Asn
                645                 650

<210> SEQ ID NO 6
<211> LENGTH: 650
<212> TYPE: PRT
<213> ORGANISM: Oryza.sativa L.

<400> SEQUENCE: 6

Met Ala Cys Leu Gln Leu Gln Val Leu Leu Leu Ala Cys Leu Leu
1               5                   10                  15
Leu Asp Ala His His Leu Ser Ser Ala Ala Thr Val Pro Thr Pro
                20                  25                  30
Pro Phe Ser Phe Asn Phe Asp Phe Ser Asn Met Ser Thr Tyr Lys Pro
        35                  40                  45
Asp Asp Leu Arg Phe Glu Gly Asn Ala Thr Val His Gly Ser Phe Val
50                  55                  60
Asp Leu Thr Cys Asn Ala Tyr Gly Leu Asp Ile Ser Gln Cys Thr Ala
65                  70                  75                  80
Gly Arg Met Ser Tyr Asn His Pro Val Pro Phe Tyr Asp Gln Thr Thr
                85                  90                  95
Lys Glu Val Ala Ser Phe Ser Thr Gln Phe Thr Phe Lys Ile Ile Val
                100                 105                 110
Pro Arg Phe Asn Asn Asp Lys Glu Lys Gly Asp Gly Met Ala Phe Phe
        115                 120                 125
Leu Ala Arg Tyr Pro Ser Arg Met Pro Pro Asp Ser Gly Gly Gly Ser
        130                 135                 140
Leu Gly Leu Ile Thr Asn Asn Asn Tyr Ser Ser Phe Gly Pro Asp Gln
145                 150                 155                 160
Phe Val Ser Val Glu Phe Asp Thr Tyr Asn Asn Thr Trp Glu Gln Pro
                165                 170                 175
Lys Gln Thr Gly Asp His Met Gly Ile Asn Ile Asn Thr Val Thr Phe
                180                 185                 190
Ser Thr Asn Thr Thr Ser Val Ser Ser Phe Ser Pro Asn Glu Ser Met
        195                 200                 205
Met Lys Ala Ser Ile Thr Phe Asp Ser Lys Thr Ser Met Leu Val Ala
        210                 215                 220
Ser Leu Gln Tyr Thr Gly Asn Tyr Ser Asn Ile Ala Pro Val Asn Val
225                 230                 235                 240
Ser Ala Lys Leu Pro Asp Pro Thr Thr Leu Leu Pro Ser Glu Val Ala
                245                 250                 255
Val Gly Phe Ser Ala Ala Thr Gly Ala Ala Phe Glu Leu His Gln Ile
                260                 265                 270
His Ser Trp Ser Phe Asn Ser Thr Ile Ala Ala Pro Gln Leu Thr Pro
        275                 280                 285
Ile Cys Arg Asn Ile Asp Ala Asp His Lys Lys Ala Ile Ala Val Gly
        290                 295                 300
```

Val Ser Ile Gly Gly Leu Ile Leu Val Leu Val Trp Ser Ile
305                 310                 315                 320

Leu Ser Trp Trp Lys Trp Arg Lys Thr Asn Arg Glu Phe Asp Lys Gly
                325                 330                 335

Thr Arg Gly Ala Cys Arg Phe Asn Tyr His His Leu Ala Ala Ala Thr
            340                 345                 350

Asn His Phe Ser Met Asp Asn Arg Ile Gly Ala Gly Ala Phe Gly Glu
                355                 360                 365

Val His Lys Gly Phe Leu Thr Gln Leu Gly Arg Glu Val Ala Val Lys
        370                 375                 380

Lys Ile Leu Arg Glu Ser Arg Ala Gly Asn Lys Asp Phe Phe Asp Glu
385                 390                 395                 400

Val Gln Thr Ile Ser Arg Ala Lys Gln Lys Asn Leu Val Glu Leu Leu
                405                 410                 415

Gly Trp Gly Met Lys Gly Ser Ser Asn Ile Ile Asp Phe Met Cys Trp
            420                 425                 430

Arg Arg Gln Lys Asn Thr Asp Leu Phe Leu Val Tyr Glu Phe Val Asp
                435                 440                 445

Asn Gly Asn Leu His Met His Leu Tyr Glu Lys Glu Ala Leu Leu Ser
        450                 455                 460

Trp Arg Ile Arg Tyr Lys Ile Val Lys Gly Ile Ile Ser Ala Leu Val
465                 470                 475                 480

Tyr Leu His His Asp Arg His Pro Tyr Ile Leu His Arg Asp Ile Lys
                485                 490                 495

Pro Ser Asn Ile Leu Leu Asp Lys Asn Phe Asn Ala Arg Leu Ala Asp
            500                 505                 510

Phe Gly Leu Ser Arg Thr Ala Asp Asn Gly Thr Ile Gln Ser Ser Met
        515                 520                 525

Val Val Gly Thr Glu Asn Tyr Leu Asp Pro Glu Cys Arg Lys Thr Gly
        530                 535                 540

Lys Phe Asn Arg Ser Ser Asp Val Phe Ser Phe Gly Leu Val Leu Leu
545                 550                 555                 560

Glu Ile Ala Cys Lys Lys Asp Glu Asn Ser Tyr Ala Gln Val Trp Glu
                565                 570                 575

Arg Tyr Ile Asp Lys Thr Leu Met Gln Ala Ala Asp Asp Arg Leu Gln
            580                 585                 590

Gly Ala Phe Asp Lys Arg Gln Met Glu Arg Val Ile Val Leu Gly Leu
        595                 600                 605

Trp Cys Cys Gln Pro Asn Ile Glu Met Arg Pro Thr Met Glu Lys Ala
        610                 615                 620

Met Asp Phe Leu Glu Ser Asp Gly Pro Leu Pro Lys Leu Ala Lys Pro
625                 630                 635                 640

Glu Ile Thr Ser Ser Ser Ala Pro Ser Asn
                645                 650

<210> SEQ ID NO 7
<211> LENGTH: 21
<212> TYPE: DNA
<213> ORGANISM: Artificial Sequence
<220> FEATURE:
<223> OTHER INFORMATION: forward primer

<400> SEQUENCE: 7
tccagagcag gaaacaagga c                                             21

```
<210> SEQ ID NO 8
<211> LENGTH: 20
<212> TYPE: DNA
<213> ORGANISM: Artificial Sequence
<220> FEATURE:
<223> OTHER INFORMATION: reverse primer

<400> SEQUENCE: 8
gcctacgcca gcacatgaaa                                              20

<210> SEQ ID NO 9
<211> LENGTH: 19
<212> TYPE: DNA
<213> ORGANISM: Artificial Sequence
<220> FEATURE:
<223> OTHER INFORMATION: guide RNA sequence

<400> SEQUENCE: 9
catctctcag tgcacggct                                               19

<210> SEQ ID NO 10
<211> LENGTH: 23
<212> TYPE: DNA
<213> ORGANISM: Artificial Sequence
<220> FEATURE:
<223> OTHER INFORMATION: target sequence

<400> SEQUENCE: 10
acatctctca gtgcacggct ggg                                          23

<210> SEQ ID NO 11
<211> LENGTH: 25
<212> TYPE: DNA
<213> ORGANISM: Artificial Sequence
<220> FEATURE:
<223> OTHER INFORMATION: Hygromycin forward primer

<400> SEQUENCE: 11
acggtgtcgt ccatcacagt ttgcc                                        25

<210> SEQ ID NO 12
<211> LENGTH: 24
<212> TYPE: DNA
<213> ORGANISM: Artificial Sequence
<220> FEATURE:
<223> OTHER INFORMATION: Hygromycin reverse primer

<400> SEQUENCE: 12
ttccggaagt gcttgacatt ggga                                         24
```